United States Patent [19]

Mori

[11] Patent Number: 4,844,579
[45] Date of Patent: Jul. 4, 1989

[54] SOLAR RAY ENERGY RADIATION DEVICE FOR USE IN MEDICAL TREATMENT

[76] Inventor: Kei Mori, 3-16-3-501, Kaminoge, Setagaya-ku, Tokyo, Japan

[21] Appl. No.: 239,051

[22] Filed: Aug. 31, 1988

Related U.S. Application Data

[63] Continuation of Ser. No. 2,098, Jan. 12, 1987, abandoned.

[30] Foreign Application Priority Data

Jan. 16, 1986 [JP] Japan ................................ 61-6974

[51] Int. Cl.⁴ .............................................. A61N 5/06
[52] U.S. Cl. .................... 350/96.10; 128/372; 128/397
[58] Field of Search ............ 350/96.10, 96.15; 128/303.1, 362, 372, 395, 396, 397, 398

[56] References Cited

U.S. PATENT DOCUMENTS

| | | | |
|---|---|---|---|
| 1,137,393 | 4/1915 | Fogg | 128/395 |
| 1,542,183 | 6/1925 | Steinberg | 350/96.1 X |
| 3,417,746 | 12/1968 | Moore et al. | 128/398 X |
| 4,287,554 | 9/1981 | Wolff | 128/396 X |
| 4,317,615 | 3/1982 | Herold | 350/96.1 X |
| 4,505,545 | 3/1985 | Salia-Munoz | 128/395 X |
| 4,600,009 | 7/1986 | Kramer et al. | 128/396 |
| 4,660,925 | 4/1987 | McCaughan, Jr. | 350/96.1 X |
| 4,690,141 | 9/1987 | Castel et al. | 128/396 |
| 4,763,971 | 8/1988 | Mori | 350/96.1 |
| 4,766,899 | 8/1988 | Mori | 128/397 |
| 4,785,811 | 11/1988 | Mori | 128/397 |
| 4,796,967 | 1/1989 | Mori | 350/96.10 |

FOREIGN PATENT DOCUMENTS 1357156 6/1974 United Kingdom ............ 350/96.10

*Primary Examiner*—John D. Lee
*Attorney, Agent, or Firm*—Jordan and Hamburg

[57] ABSTRACT

A solar ray energy radiation device for use in medical treatment, comprises a transparent or semi-transparent cylindrical member, a cover member for closing off one end surface of the cylindrical member, a covering cap member put on another end of the cylindrical member so as to be removed from and attached to the same, and an optical conductor cable having a light ray emitting end mounted on the cover member. Solar ray energy transmitted through the optical conductor cable is radiated from the light ray emitting end thereof into the cylindrical member and further radiated onto a medical treatment area by bringing the covering cap member into contact with the medical treatment area.

12 Claims, 3 Drawing Sheets

SOLAR RAY ENERGY RADIATION DEVICE FOR USE IN MEDICAL TREATMENT

This application is a continuation of application Ser. No. 002,098 filed Jan. 12, 1987, abandoned.

BACKGROUND OF THE INVENTION

The present invention relates to a solar ray energy radiation device for use in medical treatment, in particular, a light ray radiation device which radiates light ray energy that corresponds to the visible light ray components of solar rays. These light rays are directed to a diseased part of or a desired portion of a patient's body as a form of medical treatment; or are radiated onto the surface of a person's skin as a form of beauty treatment or for the promotion of a person's general health.

In recent years, a large number of persons suffer from incurable diseases such as arthritis, neuralgia and rheumatism, or from pain caused by an injury, a bone fracture or pain from an unknown cause. Furthermore, persons cannot avoid having their skin show signs of aging which progresses gradually from a comparatively young age. On the other hand, the present applicant has previously proposed focusing solar rays or artificial light rays by the use of lenses or the like, and to guide the same into an optical conductor, then to transmit them onto an optional desired place through the optical conductor. Those light rays transmitted in such a way are employed for use in illumination or for other like purposes, as for example, to cultivate plants, chlorella, or the like. In such a process, visible light rays not containing harmful ultraviolet or infrared rays, promote health and also prevent a person's skin from aging. Furthermore, the effects of those visible light rays are very noticeable in giving patients relief from arthritis, neuralgia, bedsores, rheumatism, injuries, bone fractures, or the like, as well as for alleviating pain from those same diseases. Such results have been corroborated by the present applicant's own experience.

On the basis of the afore-mentioned discovery, the present applicant has previously proposed in various ways a light ray radiation device for use in medical treatment capable of radiating the light rays that correspond to the visible light ray components of solar rays, but not containing therein harmful components such as ultraviolet rays and infrared rays.

However, in the case of performing medical treatment in such a manner that the solar ray energy radiation device for use in medical treatment is brought into contact with the skin of a patient so as to cover the diseased area or the desired portion of a patient with the same radiation device, infection may occur because of bacilli or bacteria the contact side of the radiation device in that it is very unsanitary.

On the contrary, in the case of providing the afore-mentioned radiation device individually for the respective patients and employing the same device by connecting it with the optical conductor cable and disconnecting it therefrom for every individual patient, such serious problems do not occur from a sanitary standpoint. However, the cost of employing the radiation device increases, and further, a large number of devices need to be connected with and disconnected from the optical conductor cable for every patient so that the performance efficiency turns out to be worse.

SUMMARY OF THE INVENTION

It is an object of the present invention to provide a sanitary solar ray energy radiation device for use in medical treatment, in which infection from bacilli or bacteria between patients is prevented.

It is another object of the present invention to provide a solar ray energy radiation device for use in medical treatment having a hollow covering cap member put on the device so as to be removed therefrom and attached thereto, and disposed after performing medical treatment.

The above-mentioned features and other advantages of the present invention will be apparent from the following detailed description which goes with the accompanying drawings.

DESCRIPTION OF THE PREFERRED EMBODIMENTS

Figure 1:
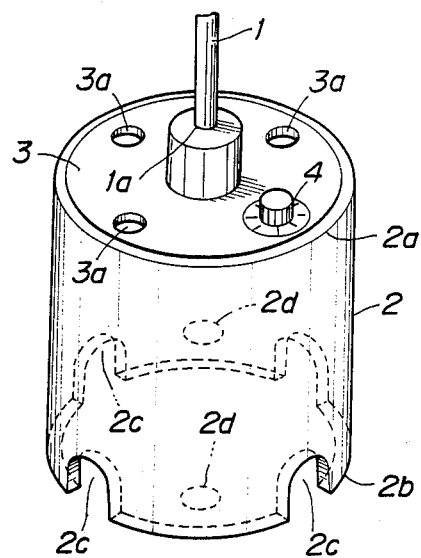
FIGS. 1 and 2 are perspective views showing an embodiment of the solar ray energy radiation device which has been previously proposed by the present applicant, respectively.

FIG. 1 is a construction view for explaining an embodiment of a light ray radiation device for use in medical treatment according to the present invention. In FIG. 1, 1 is an optical conductor cable. Solar rays or artificial light rays are guided into the optical conductor cable 1 from the end portion thereof and transmitted therethrough. The light rays (the white-colored light rays) corresponding to the visible light ray components of solar rays are transmitted through an optical conductor cable 1 in such a manner as was previously proposed in various ways by the present applicant. 2 is a semitransparent or transparent cylindrical member attached to the optical conductor cable 1 at the light ray emitting side 1a thereof, and 3 is a cover member for closing off one end 2a of the cylindrical member 2. The light ray emitting end 1a of the optical conductor cable 1 is placed at approximately the central portion of the cover member 3. Solar ray energy transmitted through the optical conductor cable 1 is channeled into the cylindrical member 2.

At the time of its use for medical treatment, another end 2b of the cylindrical member 2 is brought in line with the position for medical treatment or placed opposite the same at a desired distance. The light rays, consisting of visible light rays, transmitted through the optical conductor cable 1, as mentioned before, are focused onto a diseased part, a desired portion of a patient's body, or other various parts of the human body. As mentioned above, the light rays to be radiated onto a diseased part of a patient are light rays corresponding to the visible light ray components of solar rays which contain neither ultraviolet nor infrared rays. Thereby, it is possible to administer medical treatment without the patient suffering from any harmful effects of ultraviolet or infrared rays.

With respect to the above-mentioned light ray radiation device for use in medical treatment, since the cylindrical body 2 is constructed of a semi-transparent or transparent substance, the position of the light rays being radiated and the approximate intensity of the light rays can be assured by observing both of them with the naked eye. However, in the case of bringing the end portion 2b of the cylindrical member 2 into close contact with the diseased area or a desired portion of a patient, there is a fear that the inner wall of the cylindrical member 2 will become fogged up as a result of moisture in the form of vapor or sweat being discharged from the patient's skin, or the like, and thereby causing the interior of the cylindrical member 2 not to be visible from the outside. Furthermore, the patient's skin will not be able to breathe because the interior of the cylindrical member 2 will be filled with moisture.

In order to solve such a problem, in the case of the embodiment shown in FIG. 1, notches 2c are formed at the end portion side 2b of the cylindrical member 2 or through-holes 2d are formed on the side wall of the cylindrical member 2 so as to pass therethrough, and further, through-holes 3a are formed on the cover member 3. In such a construction, air can flow freely into the cylindrical member 2, and therefore it will be possible to prevent the interior of the cylindrical member 2 from becoming fogged up or from being filled with moisture.

Furthermore, in the case of administering medical treatment by radiating solar ray energy onto the diseased part or the desired portion of a patient as mentioned above, the time period of radiation will differ according to the condition of the patient. It is troublesome to keep watch on the radiation time period. A timer 4 is employed for setting up the above-mentioned radiation time period. The time period to be set up is recorded on a card or the like not shown in FIG. 1. For example, it is recorded thereon for every phase of the diseased condition. By referring to the card, the patient can set up the radiation time period needed. When the timer 4 measures (counts) the set time period, it sends out an alarm sound or turns on a lamp for informing the patient that the set time period has elapsed.

Figure 2:
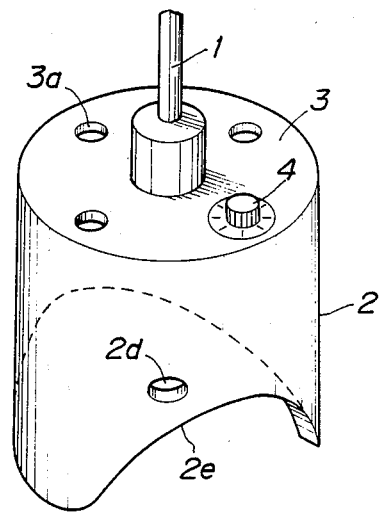

FIG. 2 is a construction view for explaining the other embodiment of a solar ray energy radiation device which has been previously proposed by the present applicant. In this embodiment, the end portion 2b of the cylindrical member 2 is formed in a shape 2e corresponding to that of a limited portion, upon which solar ray energy is administered. In the case of the embodiment shown in FIG. 2, the shape 2e is so formed that the diameter thereof coincides with that of the arm or the leg of a person. Thereby, it is possible to apply solar ray energy effectively onto the uneven skin surface of a person, namely, to radiate the same onto the diseased part of such skin surface without allowing the solar ray energy to leak outside of the device. Moreover, in FIG. 2, the part performing the same action as that in the embodiment shown in FIG. 1 is represented by the same reference numeral.

However, in the case of performing medical treatment in such a manner that the solar ray energy radiation device for use in medical treatment is brought into contact with the skin of a patient so as to cover the diseased area or the desired portion of a patient with the same radiation device, infection by bacilli or bacteria may occur between patients via the contact side of the radiation device, that is, the end portion 2b of the cylindrical member 2 in that it is very insanitary.

On the contrary, in the case of providing the aforementioned radiation device individually for the respective patients and employing the same device by connecting it with the optical conductor cable 1 and disconnecting it therefrom for every individual patient, there aren't such serious problems from a sanitary standpoint. However, the cost of employing the radiation device increases, and further, a large number of devices need to be connected with and disconnected from the optical conductor cable for every patient so that the performance efficiency turns out to be worse.

The present invention was made in consideration of the actual circumstances as mentioned above, in particular, it is a main object of the present invention is to provide a solar ray energy radiation device for use in medical treatment as mentioned above having a hollow covering cap member put on the end 2b of the cylindrical member 2 of the same device so as to be removed therefrom and attached thereto. In such a construction of the radiation device, the above-mentioned covering cap member can be employed individually for every patient and disposed after having been used for medical treatment. It follows that the radiation device can be employed sanitarily.

Figure 3:
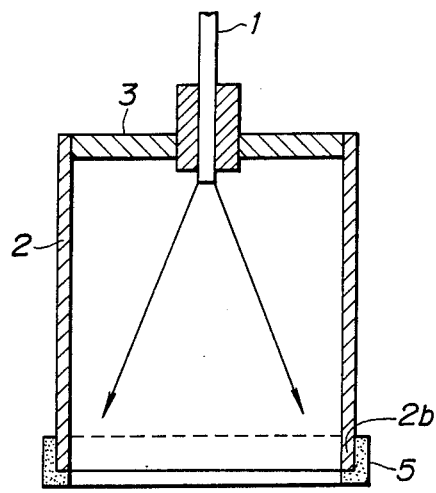
FIG. 3 is a cross-sectional view for explaining an embodiment of the present invention.

FIG. 3 is a cross-sectional view for explaining an embodiment of a solar ray energy radiation device according to the present invention. In FIG. 3, 5 is a hollow covering cap member supplemented by the present invention. The covering cap member 5 is preferable for employing the radiation device in a state of putting the covering cap member on the solar ray energy radiation device shown in FIG. 1.

Figure 4:
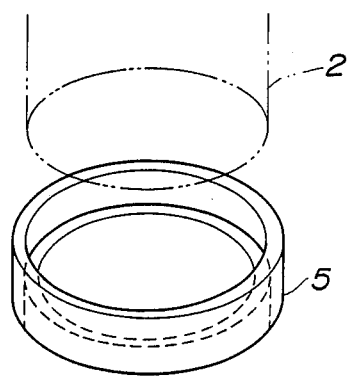
FIG. 4 is a perspective view of a covering cap member shown in FIG. 3.

FIG. 4 is a perspective view of the covering cap member 5 shown in FIG. 3. The covering cap member 5 is constructed so as to be removed from and attached to the end portion 2b of the cylindrical member 2. The covering cap member 5 is made of construction material which is low-cost, of adiabatic characteristic, light and soft, for instance, such as epispastic styrol foam, and disposed after performing medical treatment.

Figure 5:
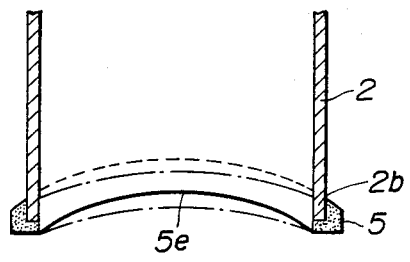
FIGS. 5 and 6 are cross-sectional views showing other embodiments of the covering cap member, respectively.

FIG. 5 is a cross-sectional view showing another embodiment of a covering cap member preferable for applying to the solar ray energy radiation device shown in FIG. 2. The covering cap member 5 is employed by putting it on the end portion side 2e of the cylindrical member 2 shown in FIG. 2. In the embodiment as shown in FIG. 5, the shape 5e of the covering cap member 5 is same as the shape 2e of the end of the cylindrical member end portion of FIG. 2. However, it is possible to form the shape 5e in an optional desired shape different from the shape 2e of the cylindrical member's end portion of the FIG. 2. In such a manner, plural kinds of cap member are prepared so that the cap member can be selectively employed in accordance with the shape of the patient's diseased part.

Figure 6:
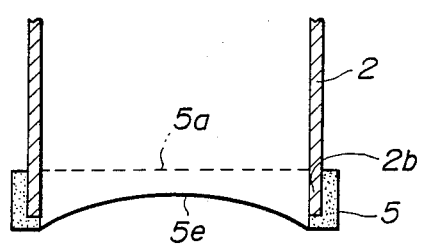

FIG. 6 is a cross-sectional view showing still another embodiment of the covering cap member 5. In the embodiment shown in FIG. 6, one end 5a of the covering cap member 5 can be employed by putting it on the end portion 2b of the cylindrical member 2 as shown in FIG. 1. When the cover member 5 is employed, it's end portion 5e comes into contact with the diseased part of the patient the same as the end portion 2e of FIG. 2.

Figure 7:
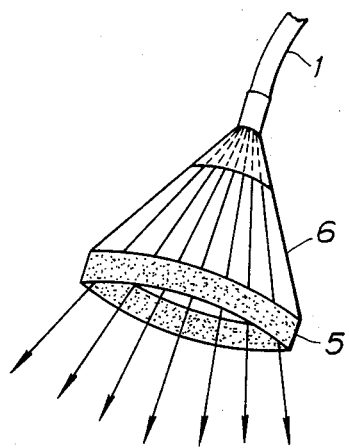
FIGS. 7 and 8 are perspective views showing still other embodiments of the covering cap member according to the present invention, respectively.
Figure 8:
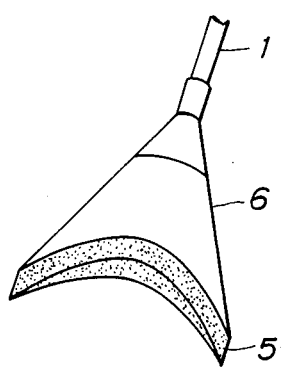

FIGS. 7 and 8 are perspective views, respectively, showing still another embodiments in which the covering cap member 5 as shown before is put on the solar ray energy radiation device for use in medical treatment employing a conical member 6 in place of the aforementioned cylindrical member 2.

As is apparent from the foregoing description, according to the present invention, a covering cap member can be put on the solar ray energy radiation device for use in medical treatment so as to be removed therefrom and attached thereto, and disposed after performing medical treatment. Consequently, it will be possible to provide a sanitary solar ray energy radiation device for use in medical treatment, wherein infection from bacilli or bacteria is not transmitted between patients.

I claim:

1. A solar-ray energy radiation device for the application of solar rays to a localized part of a person's body comprising a hood means having a circular enclosure portion with a longitudinal axis and an end closure portion on one longitudinal end of said circular enclosure portion, said circular enclosure portion being made of a transparent or a semi-transparent material, an optical conductor having a light-rays emitting end mounted on said end closure portion at a position generally aligned with the axis of said circular enclosure portion and at a position to dispose said light-rays emitting end within said hood means such that light rays emitted from said light-rays emitting end of said optical conductor pass into said hood means, said hood means confining the light rays emitted from said light-rays emitting end within said hood means, the other longitudinal end of said circular enclosure portion being open, and covering cap means removably mounted on said open end of said circular enclosure portion and operable to contact a person's body such that a part of said person's body is encircled by said covering cap means.

2. A solar-ray energy radiation device according to claim 1, wherein said circular enclosure portion comprises a cylinder.

3. A solar-ray energy radiation device according to claim 1, wherein said circular enclosure portion has a conical configuration.

4. A solar-ray energy radiation device according to claim 1, wherein said covering cap means has a generally L-shaped cross-sectional configuration having two perpendicular leg portions, one of said leg portions extending over said other longitudinal end of said circular enclosure portion, the other of said leg portions extending about the outer peripheral wall of said circular enclosure portion.

5. A solar-ray energy radiation device according to claim 1, wherein said covering cap means is made of foam material.

6. A solar-ray energy radiation device according to claim 1, wherein the other end of said circular enclosure portion is defined by an annular end face, said end face having a configuration defined by indentations extending generally in an axial direction.

7. A solar-ray energy radiation device according to claim 6, wherein said covering cap means comprises a ring member having an annular end face which has a configuration corresponding to the configuration of said annular end face of said circular enclosure portion.

8. A solar-ray energy radiation device according to claim 6, wherein said covering cap means comprises a ring member having an annular end face which has a configuration different from the configuration of said annular end face of said circular enclosure portion.

9. A solar-ray energy radiation device according to claim 6, wherein said covering cap means comprises a ring member having an annular end face defined by indentations extending generally in an axial direction, said configuration of said annular end face of said covering cap means conforming generally to the configuration of said annular end face of said circular enclosure portion.

10. A solar-ray energy radiation device according to claim 1, wherein said other end of said circular enclosure portion is defined by an end face, said end face having two generally U-shaped indentations diametrically opposed to one another, said covering cap means also having two corresponding generally U-shaped indentations diametrically opposed to one another such that said covering cap means has a configuration corresponding to the configuration of said end face, said covering cap means mating with said end face, said covering cap means receiving a person's limb during application of the device to a person's body.

11. A solar-ray energy device according to claim 1 further comprising opening means in said hood means to permit air to pass between the interior and exterior of said hood means, whereby light rays pass from said light-emitting end through the interior of said hood means to said encircled part of said person's body without leaking outside of said hood means while said opening means precludes fogging and moisture build-up within said hood means during application of the device on a person's body.

12. A solar-ray energy radiation device for the application of solar rays to a localized part of a person's body comprising a hood means having a circular enclosure portion with a longitudinal axis and an end closure portion on one longitudinal end of said circular enclosure portion, said circular enclosure portion being made of a transparent or a semi-transparent material, an optical conductor having a light-rays emitting end mounted on said end closure portion at a position generally aligned with the axis of said circular enclosure portion and at a position to dispose said light-rays emitting end within said hood means such that light rays emitted from said light-rays emitting end of said optical conductor pass into said hood means, said hood means confining the light rays emitted from said light-rays emitting end within said hood means, the other longitudinal end of said circular enclosure portion being open, covering cap means removably mounted on said open end of said circular enclosure portion operable to contact a person's body such that a part of said person's body is encircled by said covering cap means, said covering cap means comprising two generally U-shaped indentations, each of said two U-shaped indentations being diametrically opposed so as to receive a person's limb during application of the device to a person's body, a timer-alarm means on said hood means for timing the application of said solar rays to said encircled part of said person's body and for indicating an alarm after a preset amount of time has elapsed, and opening means in said hood means to permit air to pass between the interior and exterior of said hood means, whereby light rays pass from said light-emitting end through the interior of said hood to said encircled part of said person's body without leaking outside of said hood means while said opening means precludes fogging and moisture build-up within said hood means during application of the device to a person's body.

* * * * *